United States Patent [19]

Faarup

[11] 4,003,896
[45] Jan. 18, 1977

[54] METHOD OF PREPARING A SPARINGLY SOLUBLE COMPLEX OF CEPHALEXIN

[75] Inventor: Peter Faarup, Frederiksberg, Denmark

[73] Assignee: Novo Industri A/S, Denmark

[22] Filed: Dec. 17, 1974

[21] Appl. No.: 533,624

[52] U.S. Cl. .............................. 260/243 C; 424/246
[51] Int. Cl.² ....................................... C07D 501/12
[58] Field of Search ............................... 260/243 C

[56] References Cited
UNITED STATES PATENTS

| 3,862,186 | 1/1975 | Silvestri | 260/243 C |
| 3,883,519 | 5/1975 | Fujii et al. | 260/243 C |

OTHER PUBLICATIONS

Chem. Abstracts vol. 81 p. 111468a (1974).

Primary Examiner—Nicholas S. Rizzo
Attorney, Agent, or Firm—Watson, Cole, Grindle & Watson

[57] ABSTRACT

Method of recovering high purity cephalexin in high yields from a solution containing cephalexin comprising the steps of reacting said solution with a non-substituted or substituted naphthalene to form a complex with cephalexin, isolating said complex, and decomposing said complex to recover cephalexin or a salt thereof.

7 Claims, No Drawings

METHOD OF PREPARING A SPARINGLY SOLUBLE COMPLEX OF CEPHALEXIN

This invention relates to a method of preparing novel sparingly soluble cephalexin complexes, and more particularly to a method of recovering high purity cephalexin in high yields from a solution containing cephalexin.

When cephalexin, i.e. 7β-(D(—)-α-phenylglycylamido)-3-methyl-ceph-3-em-4-carboxylic acid is recovered in crystalline form from an aqueous solution thereof, it tends to occlude undesired compounds and impurities originating from the reaction mixture used for the production of said cephalexin. Thus, when cephalexin has been prepared by acylating 7-amino-3-desacetoxy cephalosporanic acid (in the following referred to as 7-ADCA) or esters thereof with phenylglycyl chloride, hydrochloride, or with other forms of protected and activated phenylglycin derivative and the protecting groups, if any, have been removed by hydrogenation or hydrolysis, the solution obtained contains undesired products or impurities originating from the starting material or decomposition products thereof, e.g. 7-ADCA and phenylglycin.

The presence of such undesired products or impurities impedes the purification of cephalexin, e.g. by disturbing the precipitation of cephalexin at its isoelectric point. Therefore, hitherto it has been difficult to prepare high purity cephalexin in high yields.

Various methods for the preparation of cephalexin complexes have been described. The specification of Danish Pat. No. 127.188 discloses a method for the preparation of a crystalline acetonitril solvate of cephalexin, and Danish patent application No. 267/72 discloses a method for the preparation of complexes of cephalosporin and N,N-dimethylformamide and N,N-dimethylacetamide. In both cases the complexing agent is used in excessive amounts (about 50% by volume or even more of the reaction mixture). Furthermore, the precipitation of the complex is effected by adjusting the pH-value of the reaction mixture at the isoelectric point of cephalexin, thus risking a co-precipitation of undesired products such as 7-ADCA and phenylglycin which have isoelectric points close to that of cephalexin.

SUMMARY OF THE INVENTION

Surprisingly, it has now been found that cephalexin is capable of forming sparingly soluble complexes in water and mixtures of water and organic solvents when cephalexin is reacted with a few equivalents of a suitable complexing agent.

The method of the invention comprises the step of reacting cephalexin with an aromatic compound comprising two aromatic nuclei.

Examples of such complexing agents are compounds having the formula:

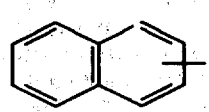

wherein R¹ is a hydrogen atom, a halogen atom, a hydroxy group, a nitro group, a non-substituted lower alkyl group, such as a methyl or an ethyl group, a substituted lower alkyl group, e.g a nitrilo-substituted alkyl group, or an alkanoyl group, such as an acetyl group.

Particularly preferred complexing agents are naphthalene; alkyl, halogen, nitro, or hydroxy substituted naphthalene; methyl-β-naphthylketone and α-naphthylacetonitril.

α- and β-Hydroxy naphthalene are particularly preferred complexing agents because the complexes formed are particularly stable, and because they are non-toxic.

The cephalexin complexes of the invention present the advantages that they can be formed during the last stage of the acylation of 7-ADCA, hydrolysable esters thereof or phosphiteamido-7-ADCA or esters thereof with phenylglycyl chloride, hydrochloride, and that they can be separated in solid form from which cephalexin can be obtained in high purity and in high yields.

The cephalexin complexes of the invention can be prepared by adding the complexing agent to the cephalexin-containing solution at a pH-value of between 2.5 and 6.0, the mole equivalent ratio of the complexing agent to cephalexin being 1–4:1 and preferably 1,5–2,5:1. Thus, it is unnecessary to adjust the pH-value of the solution to the isoelectric point of cephalexin in order to precipitate the cephalexin complex. Consequently, the above-mentioned co-precipitation of e.g. 7-ADCA and phenylglycin can be avoided.

The cephalexin complex of the invention precipitates in solid form, and the precipitate is sparingly soluble in water. Dissolved undesired compounds and impurities do not form complexes and consequently remain dissolved.

Therefore, the complex formed can easily be separated from the reaction mixture, e.g. by filtration and centrifugation.

The reaction is preferably carried out in water or in a mixture of water and a hydrophilic solvent, such as methanol, ethanol, isopropanol, acetonitril or acetone.

The cephalexin complex is formed at room temperature or at lower temperatures.

The concentration of the cephalexin contained in said solution is preferably between 1% and 20% by weight, and more preferably between 2% and 5% by weight.

Physical-chemical analyses such as NMR, IR, electrophoresis and thin-layer chromatography show that the cephalexin complexes prepared as described above contain cephalexin of a high purity.

The cephalexin complexes of the invention can be decomposed so as to form free cephalexin or salts thereof, such as sodium, potassium and magnesium salts and acid-addition salts, such as hydrochloride salts.

By suspending a cephalexin complex according to the invention in water, adding a base, such as sodium hydroxide, to the suspension, and by washing the medium thus obtained with a solvent, such as ether or butyl acetate which dissolves the complexing agent, a salt of cephalexin is obtained.

By suspending the cephalexin complex in water, acidifying the suspension so as to obtain a pH-value of about 1.5 with a strong mineral acid, such as hydrochloric acid or sulphuric acid and washing the mixture thus obtained with a solvent, such as ether or butyl acetate to remove the complexing agent, a cephalexin-acid addition salt is obtained.

In both cases, the free cephalexin is obtained by adjusting the pH-value of the solution at the isoelectric point of cephalexin, i.e. about 4.5, so as to crystallize the cephalexin from the solution.

By using a mixture of water and a solvent soluble in water, such as acetone, methanol, ethanol, isopropanol or acetonitril, the yield of the cephalexin may be improved.

Furthermore, instead of using the above-mentioned solvent which is soluble in water, 1,2-dimethoxyethane may be used as an antisolvent for cephalexin.

Preferred embodiments of the invention will now be described with reference to the following examples:

EXAMPLE 1

8.56 g (40 millimoles) of $7_R$-amino-3-methyl-3-cephem-4-carboxylic acid are suspended in 200 ml of dry methylene chloride. 11.3 ml (80 millimoles) of triethylamine are added and the mixture is cooled to 0° C. Subsequently, 5.06 ml (40 millimoles) of trimethylchlorosilane are added while stirring. The temperature is raised to room temperature over a period of 30 minutes, and the mixture is stirred for further 30 minutes. After cooling to −40° C, 3.60 ml (40 millimoles) of ethylene chlorophosphite are added. During a period of 15 minutes the temperature is raised to −10° C, and the stirring is continued for 30 minutes at said temperature.

10.72 g (52 millimoles) of D-(−)-α-phenylglycylchloride, HCl are then added to the reaction mixture, and said mixture is stirred for 5 hours at −10° C. Subsequently, 200 ml water and some ice are added, and the mixture is stirred for 30 minutes at 3°–5° C. The pH is adjusted at 7.0 with 30% sodium hydroxide solution, and the reaction mixture is filtered through Celite which is thoroughly washed with water. The organic phase is separated and the aqueous phase is washed twice with 50 ml methylene chloride. The volume of the aqueous phase is reduced to 240 ml under vacuum and pH adjusted to 5.7 with 6N hydrochloric acid. 11.53 g (80 millimoles) of β-naphthol dissolved in 20 ml ethanol are added during a period of 2 hours while stirring. Stirring is continued for about 2 hours while lowering the temperature to 5° C. Finally, the reaction mixture is left to stand overnight at 5° C. The precipitated cephalexin-β-naphthol complex and the precipitated excessive amounts of naphthol are separated by filtration and washed with water and butylacetate. A sample of the precipitate was subjected to NMR spectroscopy, and the same chemical transformations were observed as for authentic samples of cephalexin and β-naphthol. The washed precipitate is suspended in 160 ml water and 160 ml butylacetate, and the pH is adjusted at 1.5 with a 2N sulfuric acid solution. Subsequently, the mixture is filtered and the aqueous phase is washed twice with 80 ml butylacetate. The pH-value of the aqueous phase is adjusted at 4.5 with triethylamine, and the volume of the mixture is reduced under vacuum to 90 ml. 100 ml of 1,2-dimethoxyethane are added and the mixture is stirred while being cooled to 5° C over a period of about 2 hours. The mixture is left to stand overnight in a refrigerator at 5° C. The precipitate formed is separated by filtration, washed with water and dried in an exicator.

Yield: 7.0 g pure cephalexin having NMR and IR spectra which correspond exactly to those of an authentic sample of cephalexin.

EXAMPLE 2

A. 8.32 ml (80 millimoles) of diethylamine are added to 8.56 g (40 millimoles) of 7-ADCA in 50 ml dry methylene chloride, and the mixture is stirred until the 7-ADCA has been dissolved. Subsequently, 150 ml dry methylene chloride are added, and after cooling to 0° C, 5.06 ml (40 millimoles) of trimethylchlorosilane are added. The temperature is raised to 30° C, and the mixture is stirred for 30 minutes. Then the mixture is cooled to −40° C, and 3.60 ml (40 millimoles) of ethylenechlorophosphite are added. The temperature is raised to −10° C, and the mixture is stirred for 30 minutes. 9.9 g (48 millimoles) of D-(−)-α-phenylglycylchloride hydrochloride are added to the reaction mixture, and the mixture thus formed is stirred at −10° C for 4 hours. Then 300 ml water containing some ice are added, and the stirring is continued at 3°–5° C for 30 minutes.

B. The pH-value of the reaction mixture is adjusted at 7.0 by adding 30% sodium hydroxide solution. The mixture is filtered, and the organic phase is separated. The pH-value of the aqueous phase is adjusted at 5.7 with 6N hydrochloric acid, and while stirring at room temperature, a solution of 11.5 g (80 millimoles) α-naphthol in 20 ml ethanol are added dropwise. The precipitate formed is separated by filtration and washed with water and n-butyl acetate. 11.4 g of a cephalexin-α-naphthol complex are obtained. High voltage paper electroforesis showed contents of pure cephalexin with no traces of 7-ADCA and phenylglycine.

The NMR spectrum in trifluoro acetic showed the same chemical transformations as authentic samples of cephalexin and α-naphthol. The IR spectrum in KBr showed a β-lactame carbonyl band at 1750 cm$^{-1}$.

C. The complex was suspended in 40 ml water and 40 ml n-butyl acetate, and the pH-value was adjusted at 1.5 with 6N sulfuric acid, whereby the complex was dissolved. The aqueous phase was separated, and shaken twice with 50 ml n-butyl acetate. The volume was reduced in vacuum to 25 ml, and 25 ml isopropanol were added. The pH-value was adjusted at 4.7 with triethylamine, and the mixture was simultaneously seeded with cephalexinmonohydrate. The mixture was then cooled to 5° C, and the precipitate thus formed was removed by filtration, washed with isopropanol/-water (1:1) and dried.

Yield: 7.3 g cephalexinmonohydrate with NMR and IR spectra and an analysis corresponding to those of authentic cephalexinmonohydrate.

EXAMPLE 3

11.9 ml (89 millimoles) of triethylamine were added to 8.56 g (40 millimoles) of 7-ADCA suspended in 500 ml dry methylene chloride. The mixture was cooled to 5° C, and 6.0 ml (50 millimoles) dimethyl-dichlorosilane were added. The mixture was refluxed for 1 hour. Then the mixture was cooled to −2° C, and 6.7 ml (53 millimoles) of dimethylaniline were added. Subsequently, 10.7 g (52 millimoles) of D-(−)-α-phenylglycylchloride, hydrochloride were added in portions during 1 hour, and the mixture was stirred at −2° C for 3 hours. The reaction mixture was poured into 300 ml ice water, and the pH-value was adjusted at 7.0 with 30% sodium hydroxide solution. 300 ml of chloroform were added, the mixture filtered, and the organic phase separated. The aqueous phase was evaporated in vacuum to 175 ml, the pH-value adjusted at 5.7 with 6N hydrochloric acid, and while stirring, a solution of 11.5 g (80 millimoles) of β-naphthol in 20 ml acetone were added dropwise at room temperature. The precipitate formed was removed by filtration and washed with water and n-butylacetate. 14.6 g of a cephalexin-β-naphthol complex were obtained. High voltage paper electroforesis showed contents of pure cephalexin with no traces of 7-ADCA and phenylglycine. The NMR spectrum in trifluoro acetic acid showed the same chemical transformations as for authentic samples of cephalexin and β-naphthol. The IR spectrum in KBr showed a β-lactame carbonyl band at 1750 cm$^{-1}$. After treating the complex as described in Example 2,C, 10.0 g cephalexinmonohydrate were obtained.

EXAMPLE 4

The procedure disclosed in Example 2,A, was repeated, and the pH-value of the reaction mixture was adjusted at 7.0 with a 30% sodium hydroxide solution. The reaction mixture was filtered, and the organic phase was separated. The pH-value of the aqueous phase was adjusted at 5.7 with 6N hydrochloric acid, and while stirring, a solution of 13.4 g (80 millimoles) of 1-naphthyl acetonitrile in 20 ml ethanol were added dropwise at room temperature. The precipitate formed was removed by filtration and washed with water and n-butylacetate. 9.1 g of cephalexin-1-naphthyl acetonitrile complex were obtained. By high voltage paper electroforesis this product showed contents of pure cephalexin with no traces of 7-ADCA and phenylglycine. The NMR spectrum in trifluoro acetic acid showed the same chemical transformations as for authentic samples of cephalexin and 1-naphthyl acetonitrile. The IR spectrum in KBr showed a β-lactame carbonyl band at 1760 cm$^{-1}$.

After treating the complex as described in Example 2,C, 6.0 g cephalexin-monohydrate were obtained.

EXAMPLE 5

The procedure described in Example 2,A, was repeated, and the reaction mixture was filtered, and the organic phase separated. The pH-value of the aqueous phase was adjusted at 2.5 with 30% sodium hydroxide solution, and while stirring, a solution of 11.5 g (80 millimoles) of β-naphthol in 20 ml ethanol were added dropwise at room temperature. The precipitate formed was removed by filtration and washed with water and n-butyl acetate. 9.6 g of a cephalexin-β-naphthol complex were formed.

High voltage paper electroforesis showed contents of pure cephalexin with no traces of 7-ADCA and phenylglycine.

The NMR spectrum in trifluoro acetic acid showed the same chemical transformations as for authentic samples of cephalexin and β-naphthol. The IR spectrum in KBr showed a β-lactame carbonyl band at 1750 cm$^{-1}$.

After treating the complex as described in Example 2,C, 5.6 g cephalexin-monohydrate were obtained.

EXAMPLE 6

The procedure described in Example 2,A, was repeated, and the pH-value of the reaction mixture was adjusted at 7.0 with 30% sodium hydroxide solution. The solution was then filtered, and the organic phase separated. The pH-value of the aqueous phase was adjusted at 5.7 with 6N hydrochloric acid, and while stirring, 10.3 g (80 millimoles) of naphthalene in 20 ml of 1,2-dimethoxyethane were added dropwise at room temperature. The precipitate formed was removed by filtration and washed with water and n-butylacetate. 7.6 g of a cephalexin-naphthalene complex were obtained.

High voltage paper electroforesis showed contents of pure cephalexin with no traces of 7-ADCA and phenylglycine.

The NMR spectrum in trifluoro acetic acid showed the same chemical transformations as for authentic samples of cephalexin and naphthalene. The IR spectrum in KBr showed a β-lactame carbonyl band at 1760 cm$^{-1}$. After treating the complex as disclosed in Example 2,C, 5.5 g cephalexin-monohydrate were obtained.

EXAMPLE 7

The procedure disclosed in Example 2,A, was repeated, and the pH-value of the reaction mixture was adjusted at 7.0 with 30% sodium hydroxide solution. The mixture was filtered, and the organic phase separated. The aqueous phase was evaporated in vacuum to 200 ml, and 150 ml acetone were added. The pH-value was adjusted at 5.7, and a solution of 11.53 g (80 millimole) of β-naphthole in 20 ml acetone were added dropwise. The precipitate formed was removed by filtration and washed with water and n-butylacetate. 6.5 g of a cephalexin-β-naphthol complex containing pure cephalexin were obtained. After treating the complex as described in Example 2,C, 4.1 g cephalexin-monohydrate were obtained.

EXAMPLE 8

7.31 g of impure cephalexin were dissolved in 200 ml water by means of a 30% sodium hydroxide solution (pH 7.5 –8.0). The solution was filtered, and the pH-value adjusted at 5.7 with 6N hydrochloric acid. A solution of 5.8 g (40 millimoles) of β-naphthol in 10 ml acetone were added dropwise. The precipitate formed was removed by filtration and washed with water and n-butylacetate. 8.8 g of cephalexin-β-naphthol complex containing pure cephalexin were obtained. After treating said complex as described in Example 2,C, 5.8 g cephalexin-monohydrate were obtained.

EXAMPLE 9

Example 8 was repeated while using 1-nitro-naphthalene as complexing agent. 7.2 g cephalexin-1-nitro-naphthalene complex were obtained. After treating said complex as described in Example 2,C, 4.4 g cephalexin-monohydrate were obtained.

EXAMPLE 10

Example 8 was repeated by using 2-methylnaphthalene as complexing agent. 6.2 g cephalexin-2-methylnaphthalene complex were obtained. After treating said complex as described in Example 2,C, 4.0 g cephalexin-monohydrate were obtained.

EXAMPLE 11

7.31 g (20 millimoles) cephalexin-monohydrate were dissolved in 731 ml water. The pH-value was adjusted at 4.5 (thus, the solution was an 1% solution at the isoelectric point). A solution of 5.77 g (40 millimoles) of β-naphthol in 10 ml ethanol were added. The precipitate formed was removed by filtration and washed with water and n-butylacetate. 8.4 g of a cephalexin-β-naphthol complex were obtained. After treating said complex as described in Example 2,C, 5.7 g cephalexin-monohydrate were obtained.

EXAMPLE 12

3.65 g of impure cephalexin were dissolved in 75 ml water by means of 6N sulfuric acid (pH 1.8). Subsequently, the pH-value was adjusted at 3.4 with 30% sodium hydroxide solution. A solution of 3.4 g (20 millimoles) of methyl-β-naphthylketone in 10 ml acetone was added dropwise. The precipitate formed was removed by filtration and washed with water and n-butylacetate. 3.9 g of a cephalexin-methyl-β-naphthylketone complex were obtained. After treating said complex as described in Example 2,C, 2.2 g cephalexin-monohydrate were obtained.

EXAMPLE 13

A. 4.28 g (20 millimoles) of 7-ADCA were suspended in 20 ml dry methylene chloride, and 2.08 ml (20 millimoles) of diethylamine and 2.53 ml (20 millimoles) of trimethylchlorosilane were added. The mixture was stirred at 30° C for 30 minutes, and subsequently 0.45 g unconverted 7-ADCA was removed by filtration.

B. A solution of 5.5 g (22 millimoles) of N-(t-butoxycarbonyl-D-(−)α-phenylglycine, 2.2 g (22 millimoles) of triethylamine and 5 drops of N-methylmorpholine in 100 ml dry tetrahydrofurane was added dropwise to a solution of 2.1 g (22 millimoles) of methylchloroformate in 200 ml dry tetrahydrofurane cooled to −5° C. The mixture was stirred for 20 minutes at −5° C, whereafter the filtered solution obtained as described under A above was added dropwise. The mixture was stirred at −5° C for 3 hours. The reaction mixture was filtered, and the filtrate was evaporated in vacuum to dryness. the remanense was dissolved in 100 ml acetonitrile, and 7.6 g (40 millimoles) of p-toluene sulfonic acid monohydrate were added. After standing for 20 hours at room temperature, 200 ml water were added, the pH-value adjusted at 2.5 with triethylamine, and the reaction mixture was evaporated in vacuum to 100 ml. A solution of 5.8 g (40 millimoles) β-naphthol in 10 ml acetone was added dropwise. The precipitate formed was removed by filtration and washed with water and n-butylacetate. 4.4 g of a cephalexin-β-naphthol complex containing pure cephalexin were obtained. After treating said complex as described in Example 2,C, 2.6 g cephalexin-monohydrate were obtained.

EXAMPLE 14

The procedure according to Example 2,A, and B was repeated by using β-naphthol instead of α-naphthol. 10.9 g of a cephalexin-β-naphthol complex containing pure cephalexin were obtained. The complex was suspended in 40 ml water, and 40 ml n-butylacetate, and the pH-value adjusted at 8.0 with 30% sodium hydroxide solution so as to dissolve the complex. The aqueous phase was separated and shaken twice with 50 ml of n-butylacetate. The volume was reduced in vacuum to 25 ml, and 25 ml isopropanole were added. The pH-value was adjusted at 4.7 with triethylamine, while seeding with cephalexin-monohydrate. After cooling to 5° C, the precipitate formed was removed by filtration, washed with isopropanole/water (1:1) and dried.

Yield: 6.9 g cephalexin-monohydrate.

EXAMPLE 15

8.56 g (40 millimoles) of 7-ADCA were suspended in 500 ml dry methylene chloride, and 11.9 ml (89 millimoles) of triethylamine were added. While stirring, 6.0 ml (50 millimoles) of dimethyldichlorosilane were added dropwise, and the mixture was refluxed for 1 hour. The mixture was then cooled to −40° C, and 3.6 ml (40 millimoles) of ethylene-chlorophosphite were added. The temperature was raised to −2° C, and the mixture was stirred for 30 minutes. 10.7 g (52 millimoles) of D(−)α-phenylglycylchloride, hydrochloride, were then added in portions during 1 hour, and the mixture was stirred at −2° C for 3 hours. The reaction mixture was poured into 300 ml ice water, and the pH-value was adjusted at 7.0 with 30% sodium hydroxide solution. After adding 300 ml chloroform, the mixture was filtered, and the organic phase separated. The aqueous phase was evaporated in vacuum to 175 ml. The pH value was adjusted to 5.7 with 6N hydrochlorid acid, and a solution of 11.5 g (80 millimoles) of β-naphthol in 20 ml ethanol was added dropwise while stirring and at room temperature. The precipitate formed was removed by filtration and washed with water and n-butylacetane. 16.1 g of a cephalexin-β-naphthol complex were obtained. High voltage paper electroforesis showed a contents of pure cephalexin with no traces of 7-ADCA and phenylglycine. The NMR spectrum in trifluoro acetic acid showed the same chemical displacements as for authentic cephalexin and β-naphthol. The IR spectrum in KBr showed a β-lactame carbonyl band at 1750 $cm^{-1}$. After treating the complex as described in Example 2, C, 9.4 g cephalexin-monohydrate were obtained.

I claim:

1. A method of preparing a sparingly soluble complex of cephalexin, comprising the step of reacting cephalexin with a compound having the formula:

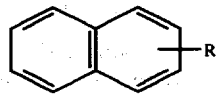

wherein R is selected from the group consisting of hydrogen, hydroxy, chlorine, nitro, methyl, -CH₂CN and -COCH₃.

2. A method according to claim 1, wherein the aromatic compound is beta-naphthol.

3. A method according to claim 1, wherein the aromatic compound is alpha-naphthol.

4. A method for recovering high purity cephalexin in high yields from a solution containing cephalexin, comprising reacting said solution with a compound having the formula:

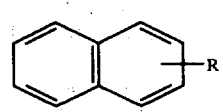

wherein R is selected from the group consisting of hydrogen, hydroxy, chlorine, nitro, methyl, —CH₂CN and —COCH₃, isolating the complex thus formed, and
decomposing the complex to recover cephalexin.

5. A method as in claim 4, further comprising the steps of decomposing the cephalexin complex in an acid or alkaline aqueous solution containing an immiscible organic solvent, separating the aqueous phase, washing the aqueous phase with the organic solvent to remove the aromatic compound, and adjusting the pH value of the solution at about the iso-electric point of cephalexin to recover cephalexin.

6. A method according to claim 5, further comprising the step of admixing the washed solution with a water-miscible solvent before adjusting the pH value of the solution.

7. A method according to claim 6, herein the water-miscible solvent is selected from the group consisting of isopropanol and 1,2-dimethoxyethane.

* * * * *